(12) United States Patent
Belov

(10) Patent No.: US 7,718,957 B2
(45) Date of Patent: May 18, 2010

(54) DYNAMIC MULTIPLEXED ANALYSIS METHOD USING ION MOBILITY SPECTROMETER

(75) Inventor: Mikhail E. Belov, Richland, WA (US)

(73) Assignee: Battelle Memorial Institute, Richland, WA (US)

(*) Notice: Subject to any disclaimer, the term of this patent is extended or adjusted under 35 U.S.C. 154(b) by 217 days.

(21) Appl. No.: 12/132,303

(22) Filed: Jun. 3, 2008

(65) Prior Publication Data
US 2009/0294644 A1 Dec. 3, 2009

(51) Int. Cl.
H01J 49/40 (2006.01)
H01J 49/26 (2006.01)
B01D 59/44 (2006.01)

(52) U.S. Cl. .............. 250/282; 250/281; 250/292; 250/288; 250/287

(58) Field of Classification Search .......... 250/282, 250/281, 288, 292, 287
See application file for complete search history.

(56) References Cited

U.S. PATENT DOCUMENTS 6,956,205 B2 * 10/2005 Park .................. 250/288
7,541,576 B2 * 6/2009 Belov et al. .......... 250/282
2008/0185513 A1 8/2008 Belov et al.
2009/0194688 A1 * 8/2009 Bateman et al. ...... 250/292
2009/0294662 A1 * 12/2009 Belov et al. .......... 250/291

* cited by examiner

Primary Examiner—Nikita Wells
(74) Attorney, Agent, or Firm—Derek H. Maughan

(57) ABSTRACT

A method for multiplexed analysis using ion mobility spectrometer in which the effectiveness and efficiency of the multiplexed method is optimized by automatically adjusting rates of passage of analyte materials through an IMS drift tube during operation of the system. This automatic adjustment is performed by the IMS instrument itself after determining the appropriate levels of adjustment according to the method of the present invention. In one example, the adjustment of the rates of passage for these materials is determined by quantifying the total number of analyte molecules delivered to the ion trap in a preselected period of time, comparing this number to the charge capacity of the ion trap, selecting a gate opening sequence; and implementing the selected gate opening sequence to obtain a preselected rate of analytes within said IMS drift tube.

5 Claims, 6 Drawing Sheets

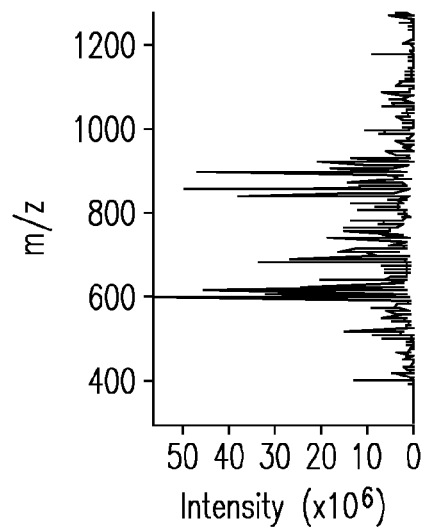 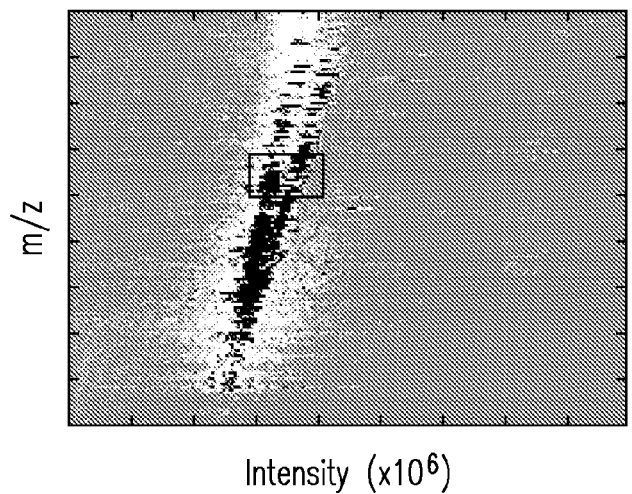
Fig. 5a          Fig. 5b
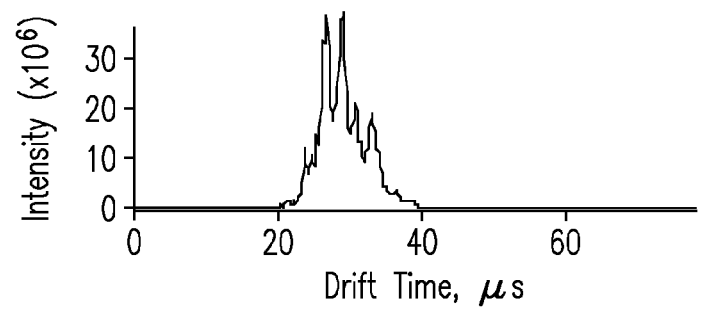
Fig. 5c

US 7,718,957 B2

DYNAMIC MULTIPLEXED ANALYSIS METHOD USING ION MOBILITY SPECTROMETER

GOVERNMENT RIGHTS

The invention was made with Government support under Contract DE-AC0676RLO 1830, awarded by the U.S. Department of Energy. The Government has certain rights in the invention.

BACKGROUND OF THE INVENTION

The enormous complexity of biological samples (e.g., from proteomics) and the need for both biological and technical analysis replicates impose major challenges for multidimensional separation platforms in regard to both sensitivity and sample throughput. A major potential attraction of the Ion Mobility Spectrometry-Time-Of-Flight-Mass Spectrometry (IMS-TOF MS) platform is the ability to provide separation speeds exceeding that of conventional condense phase separations by orders of magnitude. Known limitations of most typical IMS-TOF MS platforms that impede this attraction include the need for extensive signal averaging due to factors that include significant ion losses in the IMS-TOF interface and an ion utilization efficiency of less than ~1% with continuous ion sources (e.g., ESI).

A multiplexed IMS-TOF approach has been shown to provide up to 10-fold increase in sensitivity as compared to the conventional signal averaging approach in regard to analysis of peptide mixtures. This sensitivity improvement is based on introduction of multiple ion packets into an IMS drift tube on the time scale of a single measurement in the signal averaging experiment. Each ion packet injection occurs during a constant IMS gate open event. Ion injection process is governed by an extended pseudo-random sequence that mitigates diffusion-driven ion cloud expansion and enables efficient ion accumulation prior to each gate open event. Short (~100 us) IMS gate open events minimize contribution of the ion injection term on IMS resolving power. A complete description of this invention is found in pending U.S. patent application Ser. No. 11/701,752, entitled "Method of Multiplexed Analysis Using Ion Mobility Spectrometer" the contents of which are hereby incorporated by reference in its entirety.

The need in multiplexing the IMS-TOF is strongly dictated by the total number of analyte molecules delivered to the ion trap (preceding the IMS drift tube) per unit time and by the charge capacity of that trap. Given lower abundance signals, ion trap may remain under filled with ions in the course of IMS separation, implying no need in multiplexing to attain efficient ion utilization. In this case, ion accumulation over the entire IMS separation would be rather beneficial for achieving high sensitivity. For higher abundance ion signals, the ion trap will be over filled with ions in a fraction of IMS separation timescale, thus requiring the purging the trap multiple times throughout a single IMS separation. Therefore, a combination of approaches is needed to maximize instrument sensitivity in analysis of complex samples with broad dynamic range.

The present invention describes an approach for increasing the dynamic range of a multidimensional IMS-TOF system in analysis of biological samples. The key feature of this invention is that the multidimensional system automatically adjusts to analyte abundances in the course of experiments, providing an ultra-high sensitivity for a variety of biological samples that significantly vary in complexity and dynamic range.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

SUMMARY OF THE INVENTION

The present invention is an improvement upon the method for multiplexed analysis using ion mobility spectrometer which has been referenced and incorporated earlier in this application. In the present method, the effectiveness and efficiency of the multiplexed method is optimized by automatically adjusting rates of passage of analyte materials through an IMS drift tube during operation of said system. This automatic adjustment is performed by the IMS instrument itself after determining the appropriate levels of adjustment according to the method of the present invention.

In one embodiment of the invention, the adjustment of the rates of passage for these materials is determined by quantifying the total number of analyte molecules delivered to the ion trap in a preselected period of time, comparing this number to the charge capacity of the ion trap, selecting a gate opening sequence; and implementing the selected gate opening sequence to obtain a preselected rate of analytes within said IMS drift tube. In some embodiments the quantifying step includes performing an initial short IMS-TOF pre-scan to determine an experimental sequence, said pre-scan conducted in a signal averaging mode using constant short accumulation times (<1 ms), and comprising several IMS-TOF separations. Information obtained from this scan is then utilized to create an IMS-TOF vector from data obtained in this pre-scan. This vector is then folded and summed to obtain the total number of ions accumulated in the ion trap during the pre-scan.

Each preselected sequence from a set employed in the experiment is characterized by the number of bits, N, with the total number of gate releases per sequence equal to $2^{N-1}$ and a total sequence length of $2^N-1$. To make durations of different bit sequences similar, accumulation times per sequence are proportionally increased with a decrease in the sequence bit number. Let us elucidate this with a simple example. A 6-bit sequence has $2^6-1=63$ modulation bins, each 1 ms long. Accumulation periods throughout the sequence are constant and equal to the shortest interval between two adjacent gate open events. In the case of a 6-bit sequence, each accumulation period equals to 1 ms and the sequence duration is 63 ms. A 5-bit sequence has $2^5-1=31$ modulation bins. To compensate for the 2-fold decrease in the number of modulation bins, the duration of each bin is then increased to 2 ms. Therefore, the duration of a 5-bit sequence is 62 ms, while each accumulation period is 2 ms. Using similar logic, we would find that e.g., a 4-bit sequence is characterized by 4-ms long accumulation periods with the sequence duration of 60 ms.

Using a calibration function, the total number of ions measured in the pre-scan is converted to the optimum accumulation period of the ion trap. The optimum accumulation period is then compared against the accumulation periods of the preselected pseudo-random sequences and a sequence with the accumulation period closest to the calculated optimum is employed for signal acquisition. In one embodiment of the invention, the pseudo random sequence range extends from 1-bit extended pseudo random sequence (1 ion packet release per IMS separation) to 7-bit extended pseudo-random sequence (64 ion packet releases per IMS separation). Once the optimum sequence has been selected, the instrument then controls the gates of entry to the drift tube according to the preselected protocol. The optimum sequence is repeated for a number of pre-determined averages for signal acquisition and the instrument control system is then reset back to the pre-scan mode. In as much as this process can be repeatedly performed, this allows for increased efficiency in obtaining desired results.

The proposed design for the dynamic multiplexed IMS-TOF platform coupled to an automated LC fraction collection instrument will enable a complete 3D sample analysis in <10 min at an IMS duty cycle of >50% and a mass accuracy of <5 ppm. This approach will result in automated analysis of >100 technical replicate analyses per day. In addition, the same approach will provide high sensitivity fragmentation data and complete sequence information for biologically regulated species. The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions, we have shown and described only the preferred embodiment of the invention, by way of illustration of the best mode contemplated for carrying out the invention. As will be realized, the invention is capable of modification in various respects without departing from the invention. Accordingly, the drawings and description of the preferred embodiment set forth hereafter are to be regarded as illustrative in nature, and not as restrictive.

BRIEF DESCRIPTION OF THE DRAWINGS

FIGS. 5a-5c show a signal that was encoded with 5-bit extended pseudo-random sequence described in the present invention.

DETAILED DESCRIPTION OF THE PREFERRED EMBODIMENTS

Figure 1:
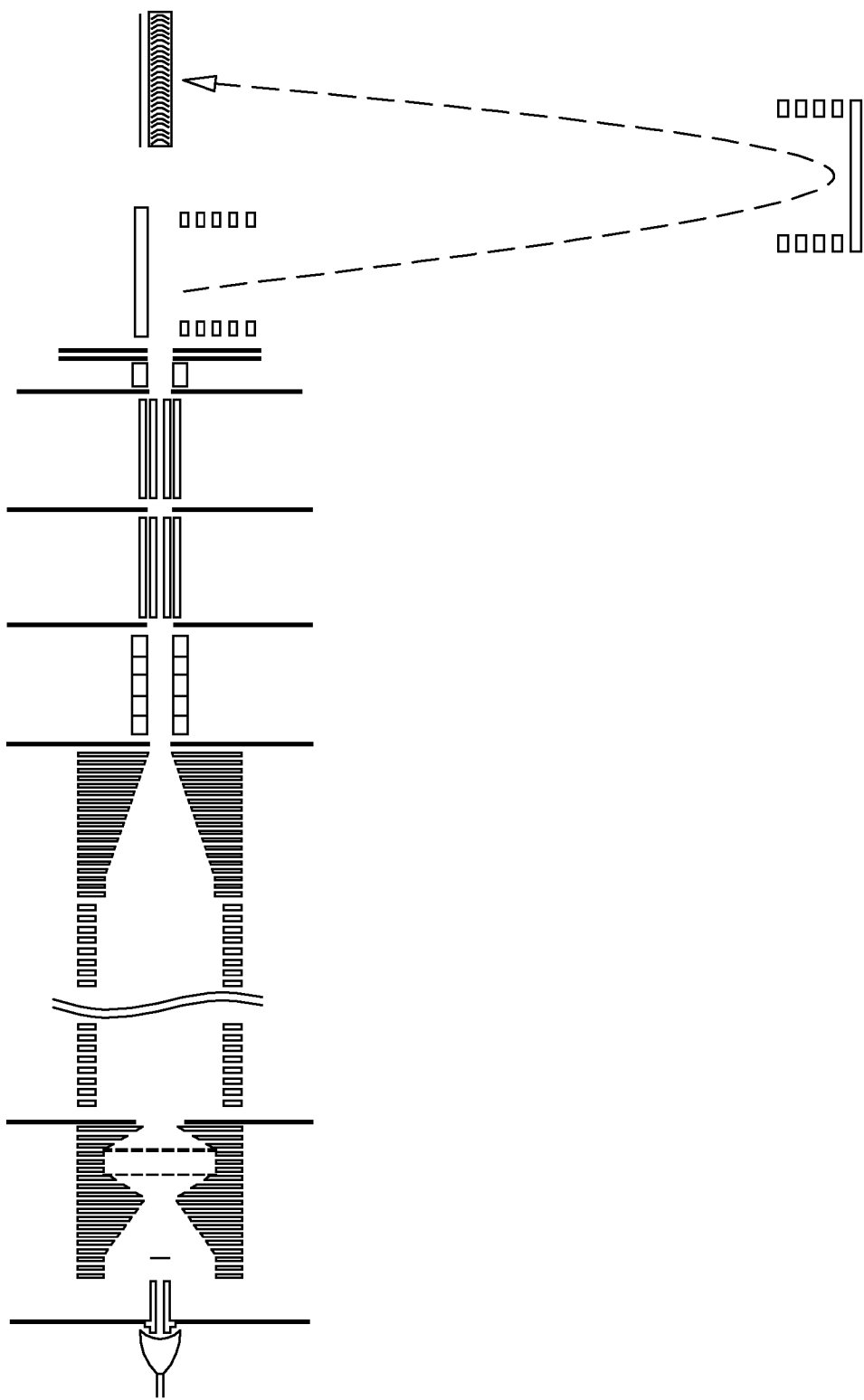
FIG. 1 shows the schematic of an IMS-TOFMS instrument used in dynamic multiplexing experiments.

The following description includes a preferred best mode of one embodiment of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

As has been discussed previously, a multiplexed IMS-TOF approach has been shown to provide up to 10-fold increase in sensitivity as compared to the conventional signal averaging approach in regard to analysis of peptide mixtures. This sensitivity improvement is based on introduction of multiple ion packets into an IMS drift tube on the time scale of a single measurement in the signal averaging experiment. Each ion packet injection occurs during a constant IMS gate open event, and the ion injection process is governed by an extended pseudo-random sequence that mitigates diffusion-driven ion cloud expansion and enables efficient ion accumulation prior to each gate open event. Short (~100 us) IMS gate open events minimize contribution of the ion injection term on IMS resolving power.

The need in multiplexing the IMS-TOF is strongly dictated by the total number of analytes molecules delivered to the ion trap (preceding the IMS drift tube) per unit time and by the charge capacity of that trap. Given lower abundance signals, ion trap may remain under filled with ions in the course of IMS separation, implying no need in multiplexing to attain efficient ion utilization. In this case, ion accumulation over the entire IMS separation would rather be beneficial for achieving high sensitivity. One the other hand, if accumulated on the timescale of IMS separation, higher abundance ion species may result in the over filling of the ion trap, implying the need for multiple ion releases from the trap per single IMS separation to achieve high sensitivity and dynamic range. In addition, the over filling of the ion trap may result in a number of undesired effects, including ion discrimination and fragmentation. Therefore, a combination of approaches is needed to maximize instrument sensitivity in analysis of complex samples with broad dynamic range.

In one embodiment, the present invention is employed with fully automated fast sample fractionation, using either strong cation/anion exchange (SCX/SAX), reverse phase (RP) capillary liquid chromatography (LC) or capillary electrophoresis (CE) separations. LC/CE separation timescale determines the analysis time. Analysis of each fraction is accomplished in two steps, first an initial short IMS-TOF pre-scan is employed to determine the experimental sequence. Secondly, a longer full IMS-TOF scan to acquire data takes place. Each IMS-TOF pre-scan is typically be conducted in the signal averaging mode using constant short accumulation times (<1 ms) to ensure that operation of the ion trap in the linear dynamic range for higher concentration fractions takes place. Following several 60-ms long IMS-TOF separations (e.g., 600-ms pre-scan), an IMS-TOF vector is folded and summed to obtain the total number of ions accumulated in the ion trap during the pre-scan. This information is then used to select the optimum sequence for the following full IMS-TOF scan. In a preferred embodiment a range of sequences from signal averaging mode (1 ion packet release per IMS separation) to 7-bit extended pseudo-random sequence (64 ion packet releases per IMS separation) is loaded in SDRAM and a particular sequence is chosen based upon the total ion signal from the pre-scan.

FIG. 1 shows the IMS-TOFMS instrument which was employed in dynamic multiplexing experiments. Electrospray-generated ions were accumulated in the ion funnel trap between the entrance and trapping grids, and then released into the IMS drift tube in short pulses. Following IMS separation, ion packets were analyzed with a TOF mass spectrometer.

Figure 2A:
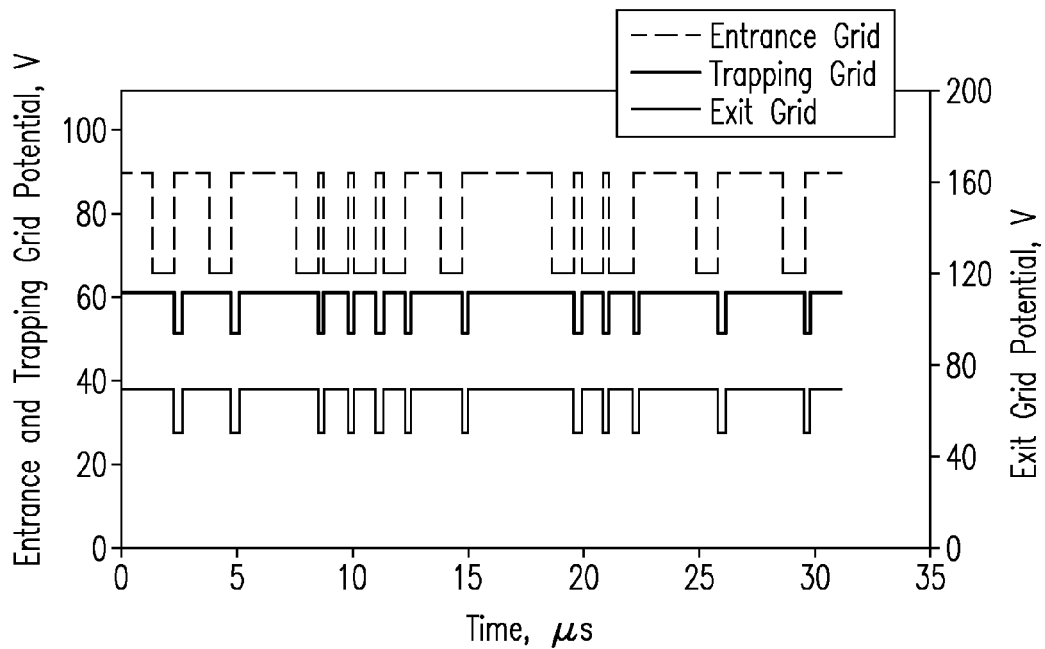
FIGS. 2a-2b show the modulation waveforms that were applied to the ion trap end-cap electrodes (i.e., grids) to introduce ions into the accumulation region of the ion trap, block ions from the continuous ion source and extract accumulated ion packets from the ion trap into the IMS drift tube
Figure 2B:
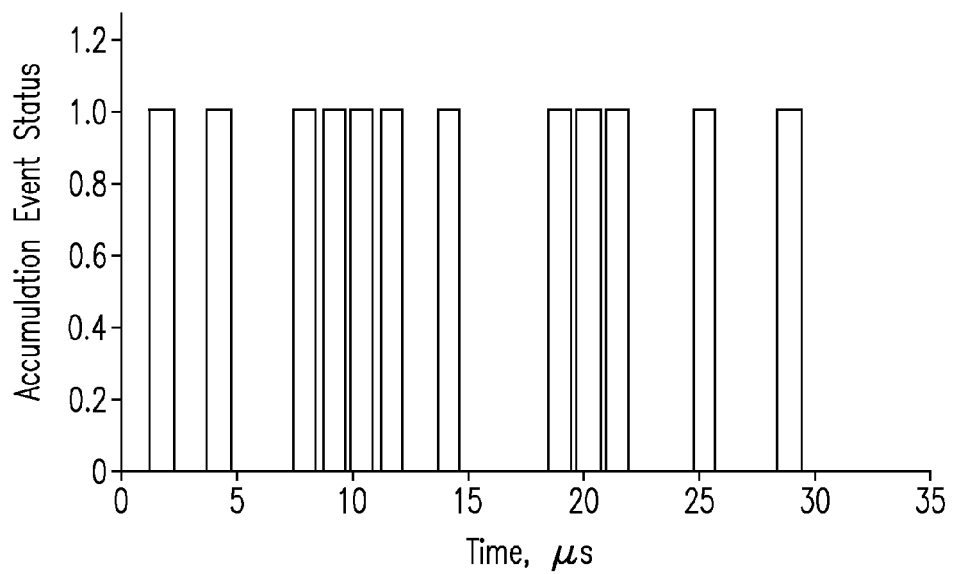

FIG. 2A shows the modulation waveforms applied to the entrance, trapping and exit grids of the ion funnel trap for encoding ion packet introduction into the IMS drift tube. Lower voltage levels in each waveform correspond to the transmission mode while higher voltage levels indicate ion beam blocking. As seen in FIG. 2A, ions from the continuous source were accumulated in the ion funnel trap for short intervals (lower voltage level at the entrance grid and high voltage level at the trapping and exit grids) and then ejected from the trap in short release pulses (high voltage level at the entrance grid and low voltage level at the trapping and entrance grid). The timing for the repetitive ion accumulation/ejection process was determined by the encoding pseudo-random sequence. As shown in FIG. 2B, ion accumulation intervals in the ion trap were constant throughout IMS-TOFMS separation. This enabled signal reconstruction without the use of complex weighing functions and made inverse transform procedure robust and applicable to signals of arbitrary complexity. The duration of the accumulation intervals was determined by the encoding sequence, and, therefore, would vary upon its alternation.

Figure 3:
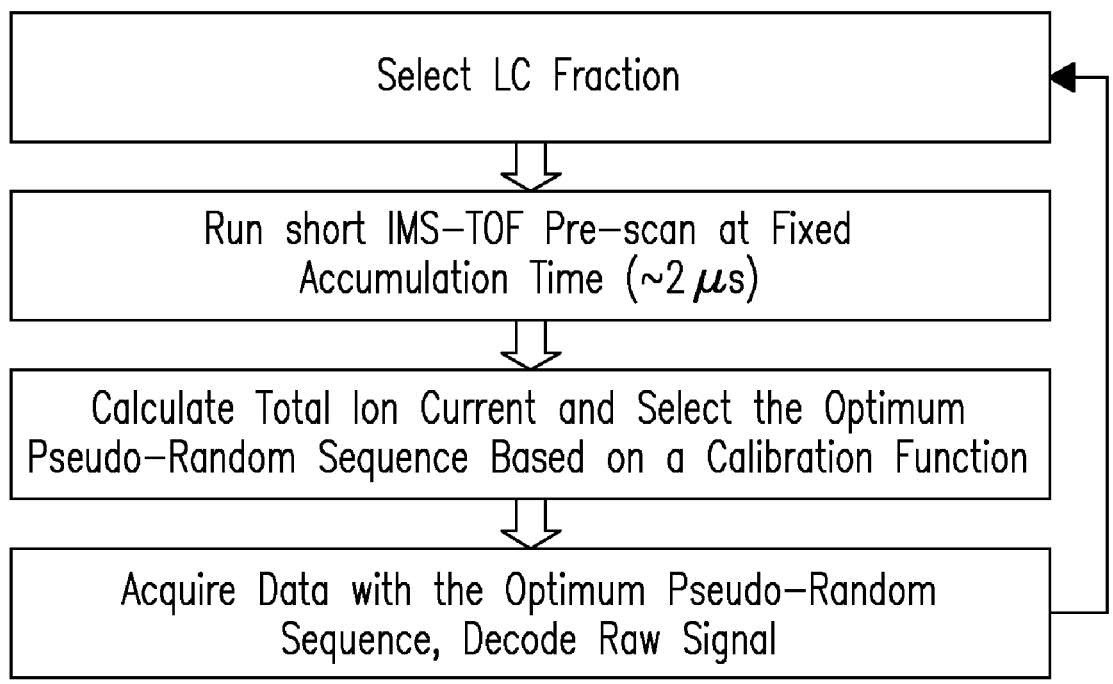
FIG. 3 shows the flow control diagram of the dynamic multiplexing experiment

FIG. 3 shows the flow control diagram for the dynamic multiplexed experiments, which can be conducted with any online or off-line condensed-phase separation, including capillary LC, SCX/SAX and CE. Each measurement is preceded by a short pre-scan that is used to determine the total ion signal at a given time during condensed-phase separation. Based on the total ion signal from the pre-scan, the optimum encoding sequence is selected from a set of pre-determined sequences using a calibration function. IMS-TOFMS experiment is then performed under the optimized conditions for a desired number of averages, and the system is reset to the pre-scan mode for the following IMS-TOFMS acquisition.

Figure 4A:
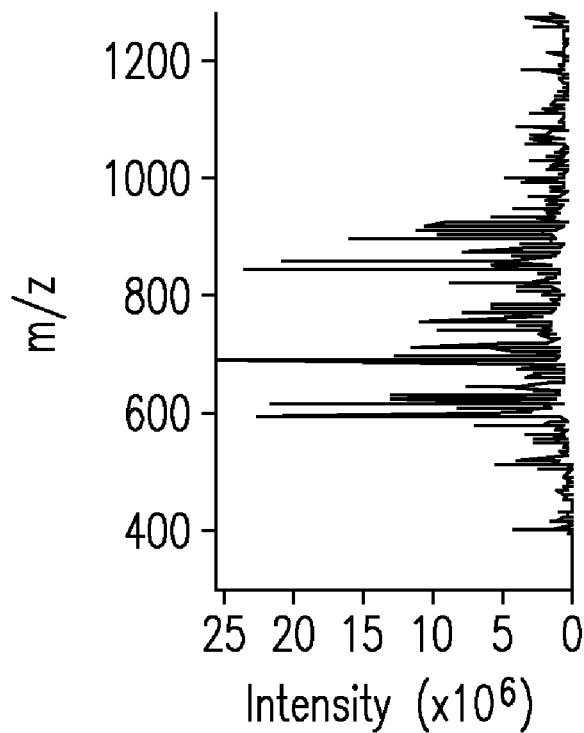
FIGS. 4a-4b show two dimensional contours along with IMS and mass spectra of the encoded and reconstructed peptide signals from depleted human plasma sample obtained under the present method. A) Signal from fraction 14 using 5 bit encoding sequence; B) Reconstructed signal from data in A); C) Signal from fraction 7 using signal averaging acquisition.
Figure 4B:
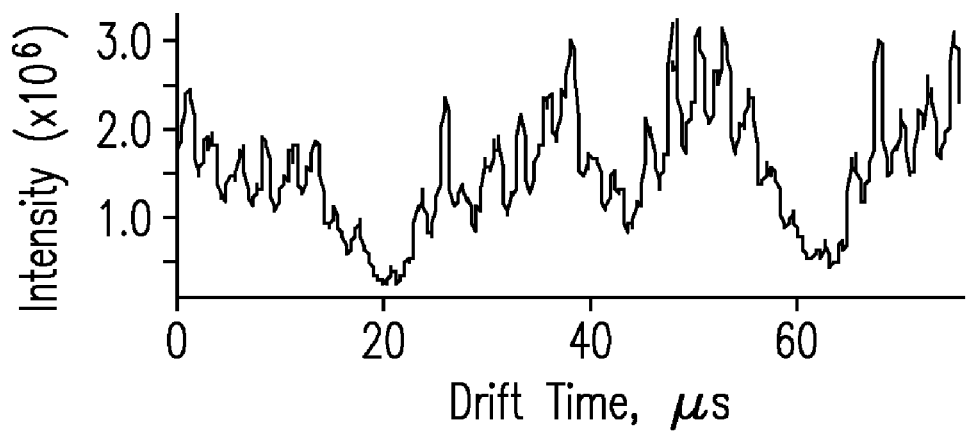

In one example, the low abundance fractions for the entire IMS separation time scale are used to accumulate ions in the trap, whereas higher bit sequence (and shorter ion accumulation times) are employed for analysis of higher abundance fractions. Referring now to FIG. 4, FIG. 4 shows reconstructed multiplexed IMS-TOF spectra obtained with two different reverse-phase fractions of a 0.5 mg/mL depleted human blood plasma sample. The spectra were acquired in a fully automated experiment using a set of 25 reverse-phase fractions. FIG. 4A shows the two-dimensional contour, IMS and summed mass spectra of the IMS-TOFMS signal encoded with a 5-bit pseudo-random sequence. Data were obtained with fraction 14 of the depleted human blood plasma sample. FIG. 4B displays the reconstructed signal using data in FIG. 4A. FIG. 4C shows the two-dimensional contour, IMS and summed mass spectra recorded in the signal averaging mode. This signal was obtained in analysis of fraction 7. FIG. 4 shows that in correlation with analyte concentrations from a particular fraction, ion accumulation times in the analysis of different fractions was be varied by a factor of 30 that helped address the dynamic range challenge. It should be noted that process allows dynamic multiplexed IMS-TOF experiments on a sample fraction to be performed during collection of the next fraction. Thus fraction collection and data acquisition/analysis overlay. This results in high throughput. For example, a complete 3D analysis of 25 reverse-phase fractions was be conducted in 15 min, with 0.2 min signal averaging in the multiplexed mode per fraction at a duty cycle of >50%. The use of data compression and developed algorithms for the reconstruction of multiplexed IMS-TOF raw vector also enabled on-line signal monitoring and quality control.

In one application, the detected features reveal statistically different abundance ratios as a result of various biological stimuli (e.g., comparison of blood plasma samples from cancer and healthy patients) will be subjected to tandem MS experiments. Using LC fraction and IMS drift time information, an RF-only ion guide positioned downstream of the IMS drift tube will be dynamically biased using a pseudo-random binary sequence identical to that employed to detect the features of interest and tailored in time to match the drift time of the features of interest. As a result, a multiplexed IMS-MS/MS spectrum corresponding to the interesting species will be detected and then reconstructed with the same algorithm as that used for deciphering parent ion spectra. Fragment correlation to precursor ions and the following identification can be performed by matching the IMS drift time profiles of parent and fragment signals, and then applying commercially available search engines such as X!Tandem or Mascot that invoke mass accuracy information.

Figure 6A:
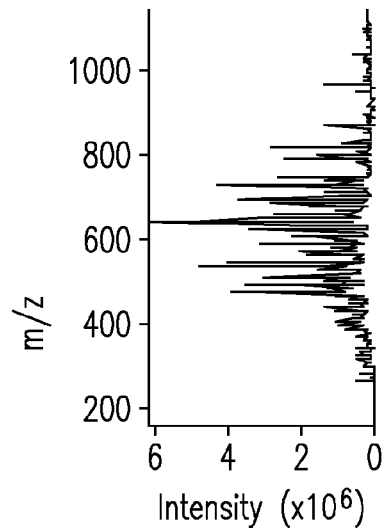
FIGS. 6a-6c show an extracted ion chromatogram corresponding to the IMS-TOF signal in FIG. 2.
Figure 6B:
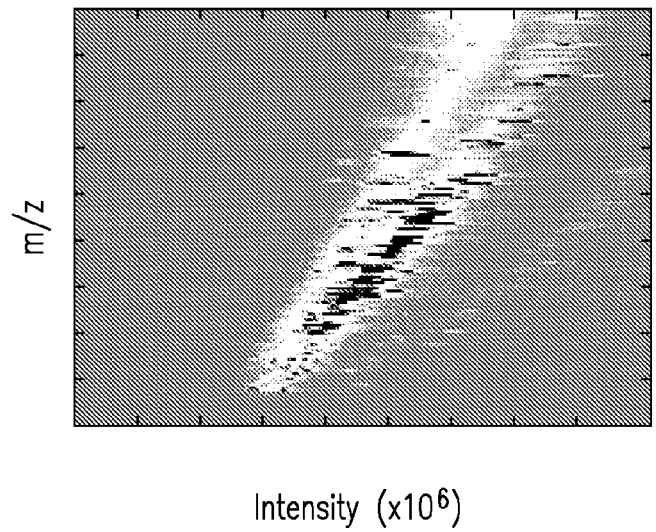
Figure 6C:
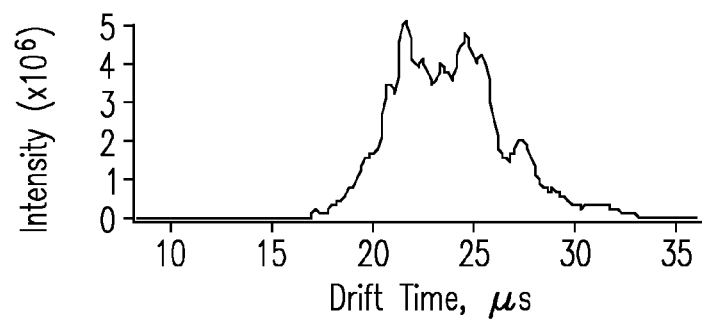

FIGS. 5 and 6 show reconstructed multiplexed IMS-TOF spectrum of a 50 nM solution of tryptic digest of bovine serum albumin. FIG. 2 shows a signal that was encoded with 5-bit extended pseudo-random sequence. FIG. 3 shows an extracted ion chromatogram of a tryptic peptide of bovine serum albumin (m/z 488.753) corresponding to the IMS-TOF signal in FIG. 2. As well as an excitation waveform applied to an RF-only multipole to activate collisional dissociation of this peptide. Activation is accomplished by biasing the multipole to lower DC potential that results in an increase in the precursor ion kinetic energy and the fragmentation shown in FIG. 6.

The described design for a dynamic multiplexed IMS-TOF platform coupled to an automated LC fraction collection instrument will enable a complete 3D sample analysis in <10 min at an IMS duty cycle of >50% and a mass accuracy of <5 ppm. This approach will result in automated analysis of >100 technical replicate analyses per day. In addition, the same approach will provide high sensitivity fragmentation data and complete sequence information for biologically regulated species.

While various preferred embodiments of the invention are shown and described, it is to be distinctly understood that this invention is not limited thereto but may be variously embodied to practice within the scope of the following claims. From the foregoing description, it will be apparent that various changes may be made without departing from the spirit and scope of the invention as defined by the following claims.

What is claimed is:

1. A method for increasing the dynamic range of a multi-dimensional IMS-TOF system comprises the steps of automatically adjusting rates of passage of analyte materials through an IMS drift tube during operation of said system; an ion trap to which a total number of analyte molecules are delivered; quantifying the said total number of analyte molecules delivered to said ion trap in a preselected period of time; comparing this number to the charge capacity of the ion trap; selecting a gate opening sequence; and implementing the selected gate opening sequence to obtain a preselected rate of analytes within said IMS drift tube.

2. The method of claim 1 wherein said quantifying step is comprised of: performing an initial short IMS-TOF pre-scan to determine an experimental sequence, said pre-scan conducted in a signal averaging mode using constant short accumulation times (<1 ms), and comprising several IMS-TOF separations creating an IMS-TOF vector from data obtained in said pre-scan; and folding and summing said vector to obtain the total number of ions accumulated in the ion trap during the pre-scan.

3. The method of claim 2 wherein said selecting step comprises:

matching a predesignated pseudo random sequence in a preselected range with the total number of ions accumulated in the ion trap during the pre-scan according to a preselected criteria.

4. The method of claim 3 wherein the pseudo random sequence range extends from 1-bit extended pseudo random sequence (1 ion packet release per IMS separation) to 7-bit extended pseudo-random sequence (64 ion packet releases per IMS separation).

5. The method of claim 3 further comprising the step of conducting a targeted MS/MS experiment by fragmenting precursor ions of interest in an RF ion guide downstream of an IMS drift tube using the same pseudo random sequence as that employed for precursor signal encoding but delayed by the drift time of the species of interest.

* * * * *

UNITED STATES PATENT AND TRADEMARK OFFICE
CERTIFICATE OF CORRECTION

| | | |
|---|---|---|
| PATENT NO. | : 7,718,957 B2 | Page 1 of 1 |
| APPLICATION NO. | : 12/132303 | |
| DATED | : May 18, 2010 | |
| INVENTOR(S) | : M Belov | |

It is certified that error appears in the above-identified patent and that said Letters Patent is hereby corrected as shown below:

Column 1, lines 7 through 10 should read:

The invention was made with Government support under grant number CA126191 from the U.S. National Institutes of Health and contract DE-AC05-76RL01830 awarded by the US Department of Energy. The government has certain rights in the invention.

Signed and Sealed this
Twenty-seventh Day of November, 2012

David J. Kappos
*Director of the United States Patent and Trademark Office*